United States Patent
Kojima et al.

(10) Patent No.: US 11,571,125 B2
(45) Date of Patent: Feb. 7, 2023

(54) LINE-OF-SIGHT MEASUREMENT DEVICE

(71) Applicants: AISIN CORPORATION, Kariya (JP); TOYOTA JIDOSHA KABUSHIKI KAISHA, Toyota (JP)

(72) Inventors: Shin-ichi Kojima, Nagakute (JP); Shin Osuga, Kariya (JP); Takashi Kato, Kariya (JP); Yuya Yamada, Kariya (JP); Takeshi Matsumura, Toyota (JP)

(73) Assignees: AISIN CORPORATION, Kariya (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 184 days.

(21) Appl. No.: 16/787,332

(22) Filed: Feb. 11, 2020

(65) Prior Publication Data
US 2020/0305712 A1     Oct. 1, 2020

(30) Foreign Application Priority Data
Mar. 28, 2019     (JP) .............................. JP2019-064828

(51) Int. Cl.
*A61B 3/15*     (2006.01)
*A61B 3/00*     (2006.01)
*G06V 40/19*     (2022.01)

(52) U.S. Cl.
CPC ............ *A61B 3/158* (2013.01); *A61B 3/0008* (2013.01); *G06V 40/19* (2022.01)

(58) Field of Classification Search
CPC ..... A61B 3/158; A61B 3/008; G06K 9/00604
See application file for complete search history.

(56) References Cited

U.S. PATENT DOCUMENTS 5,471,542 A * 11/1995 Ragland ................ A61B 3/113
                                                          351/208
8,885,882 B1 * 11/2014 Yin ..................... G06K 9/00248
                                                          382/103
(Continued)

FOREIGN PATENT DOCUMENTS

EP     3 413 234 A1     12/2018
EP     3413234 A1 *   12/2018   ........... G06K 9/0061
(Continued)

OTHER PUBLICATIONS

Communication dated Aug. 26, 2020 from European Patent Office in EP Application No. 20157854.9.
(Continued)

*Primary Examiner* — William R Alexander
*Assistant Examiner* — Sharrief I Broome
(74) *Attorney, Agent, or Firm* — Sughrue Mion, PLLC

(57) ABSTRACT

A line-of-sight measurement device includes: an imaging unit that images a face of a subject; a light illumination unit that illuminates light to an eye of the subject; a camera coordinate system eyeball center coordinate calculation unit that estimates coordinates of an eyeball center, from a face image imaged by the imaging unit; a pupil center calculation unit that estimates coordinates of an apparent pupil center, from a pupil center position on the face image; an eyeball position orientation estimation unit that calculates an optical axis vector toward the pupil center from the eyeball center on the basis of the coordinates of the eyeball center and the apparent pupil center; a corneal reflection image calculation unit that obtains coordinates of a corneal reflection image on the basis of the coordinates of the eyeball center, the optical axis vector, and a predetermined eyeball model; and an image coordinate calculation unit that estimates image coor-
(Continued)

dinates of a corneal reflection image on the face image, from the coordinates of the corneal reflection image.

6 Claims, 9 Drawing Sheets

(56) References Cited

U.S. PATENT DOCUMENTS

| | | | | |
|---|---|---|---|---|
| 2003/0123027 | A1* | 7/2003 | Amir | G06K 9/00604 |
| | | | | 351/209 |
| 2006/0110008 | A1* | 5/2006 | Vertegaal | G06T 7/251 |
| | | | | 382/103 |
| 2014/0055342 | A1* | 2/2014 | Kamimura | G06F 3/013 |
| | | | | 345/156 |

FOREIGN PATENT DOCUMENTS

| | | |
|---|---|---|
| JP | 2014-188322 A | 10/2014 |
| JP | 2017-111746 A | 6/2017 |
| JP | 2019-000135 A | 1/2019 |

OTHER PUBLICATIONS

Makota Noshiro, "Biological Measurement and Neuropsychology", Chapter 3 in http://www.ieice-hbkb.org/files/S3/S3gun_10 hen_03.pdf, 2013, 21 pages.

* cited by examiner

LINE-OF-SIGHT MEASUREMENT DEVICE

CROSS REFERENCE TO RELATED APPLICATIONS

This application is based on and claims priority under 35 U.S.C. § 119 to Japanese Patent Application 2019-064828, filed on Mar. 28, 2019, the entire contents of which are incorporated herein by reference.

TECHNICAL FIELD

This disclosure relates to a line-of-sight measurement device, and more particularly, to a line-of-sight measurement device that measures a line of sight from an image obtained by capturing an image of a face.

BACKGROUND DISCUSSION

In the related art, there is a known method of calculating eye motion by capturing a Purkinje image moving in parallel with the eye motion through a video camera or a CCD camera since the center of curvature of the cornea and the center of rotation of the eyeball are different ("Biological Measurement and Neuropsychology" (Makoto Noshiro, Chapter 3 in http://www.ieice-hbkb.org/files/S3/S3gun_10 hen_03.pdf)). A method of using an image obtained by reflection from the front surface of the cornea is a corneal reflection method.

There is a known technique capable of detecting a corneal reflection image in distinction from reflection of glasses by using a plurality of light sources or by changing a projection pattern over time (for example, JP 2014-188322A and JP 2017-1111746A).

In JP 2014-188322A, an infrared light pattern is used, and in JP 2017-1111746A, a plurality of light sources are used.

As in the technique described in "Biological Measurement and Neuropsychology" (Makoto Noshiro, Chapter 3 in http://www.ieice-hbkb.org/files/S3/S3gun_10 hen_03.pdf), in a method of using a single light source, it is difficult to distinguish between disturbance light reflected on glasses and a corneal reflection image.

In addition, the techniques described in JP 2014-188322A and JP 2017-1111746A require a device for using a plurality of light sources and light projection patterns in order to obtain a corneal reflection image. As a result, there is an increase in costs for the device.

Thus, a need exists for a line-of-sight measurement device which is not susceptible to the drawback mentioned above.

SUMMARY

A line-of-sight measurement device according to a first aspect of this disclosure includes: an imaging unit that images a face of a subject to be observed; a light illumination unit that illuminates light to an eye of the subject to be observed; a camera coordinate system eyeball center coordinate calculation unit that estimates three-dimensional coordinates of an eyeball center in a camera coordinate system, from a face image representing the face imaged by the imaging unit; a pupil center calculation unit that estimates three-dimensional coordinates of an apparent pupil center in the camera coordinate system, from a pupil center position of the eye on the face image; an eyeball position orientation estimation unit that calculates a three-dimensional optical axis vector toward a three-dimensional position of the pupil center from a three-dimensional position of the eyeball center, in the camera coordinate system, on the basis of the three-dimensional coordinates of the eyeball center in the camera coordinate system and the three-dimensional coordinates of the apparent pupil center in the camera coordinate system; a corneal reflection image calculation unit that obtains three-dimensional coordinates of a corneal reflection image in the camera coordinate system, on the basis of the three-dimensional coordinates of the eyeball center in the camera coordinate system, the optical axis vector, and a predetermined three-dimensional eyeball model; and an image coordinate calculation unit that estimates image coordinates of a corneal reflection image on the face image, from the three-dimensional coordinates of the corneal reflection image in the camera coordinate system.

BRIEF DESCRIPTION OF THE DRAWINGS

The foregoing and additional features and characteristics of this disclosure will become more apparent from the following detailed description considered with the reference to the accompanying drawings, wherein.

DETAILED DESCRIPTION

Hereinafter, embodiments disclosed here will be described in detail with reference to the drawings. The present embodiment will describe an exemplary case where the aspect of this disclosure is applied to a line-of-sight measurement device that estimates a line-of-sight vector from a captured face image.

Overview of Embodiment Disclosed Here

The line-of-sight detection technique based on the corneal reflection method is mainly handled in the embodiment disclosed here, but an overview of the eyeball model fitting method will be described for the following description.

Figure 11:
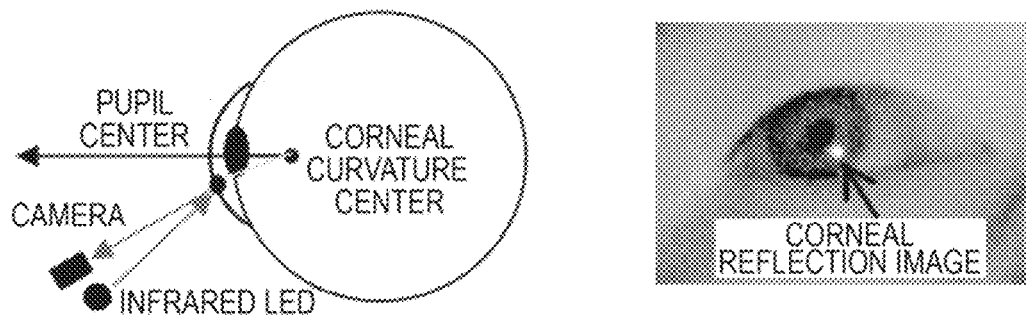
FIG. 11 is a diagram for explaining a line-of-sight detection method using a corneal reflection method.

The corneal reflection method is a method of obtaining a line-of-sight vector from a positional relationship between a pupil and a near-infrared LED (corneal reflection image) reflected in the cornea by using a camera and the near-infrared LED, as shown in FIG. 11.

Figure 12:
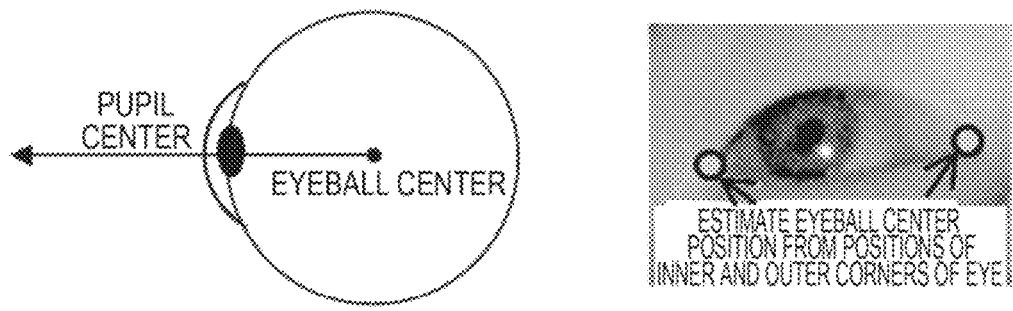
FIG. 12 is a diagram for explaining a line-of-sight detection method using an eyeball model fitting method.

The eyeball model fitting method is a method of estimating the eyeball center position by applying a three-dimensional eyeball model to the feature points of the outer corner and the inner corner of the eye as shown in FIG. 12 and setting a vector connecting the eyeball center and the pupil center as a line-of-sight vector. It is not indispensable to use the feature points of the outer corner and the inner corner of the eye, and a method of estimating the eyeball center by some means may be used.

Figure 13:
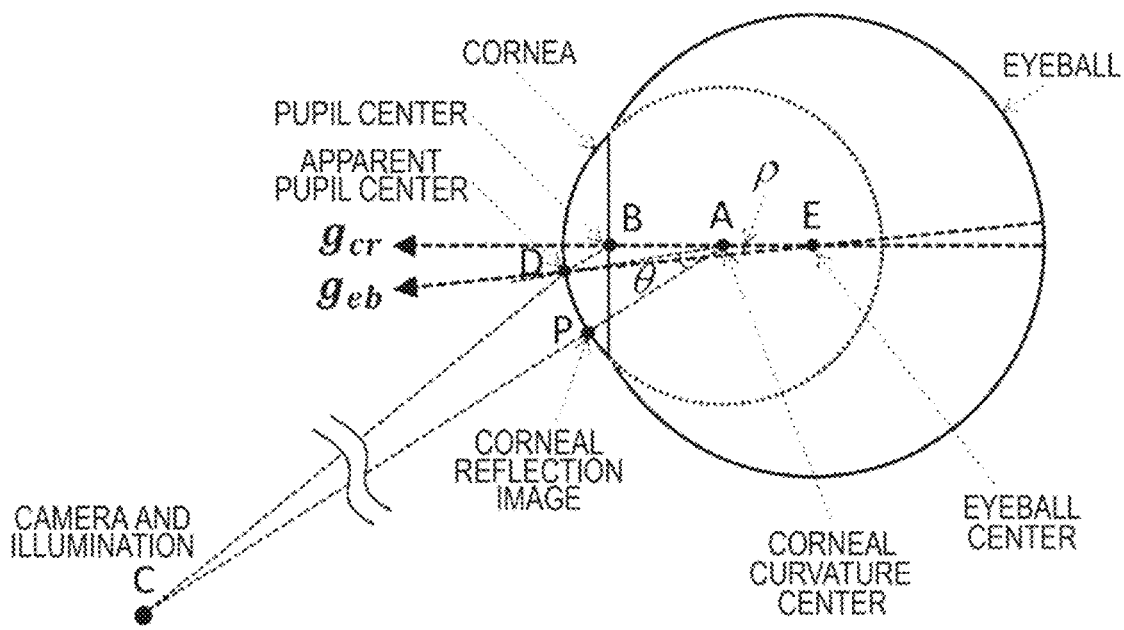
FIG. 13 is a diagram for explaining a difference between a line-of-sight vector obtained by a corneal reflection method and a line-of-sight vector obtained by an eyeball model fitting method.

FIG. 13 is a detailed explanatory diagram of the line of sight obtained by two types of line-of-sight detection methods. The line-of-sight vector obtained by the corneal reflection method is gcr, and the line-of-sight vector obtained by the eyeball model fitting method is geb. In the corneal reflection method, the coordinates of the corneal curvature center can be obtained by calculation. Therefore, as information relating to the cornea, the following three information pieces are obtained: the corneal reflection image, the corneal curvature center, and the pupil center observed on the corneal surface (hereinafter referred to as the apparent pupil center). Therefore, refraction of light at the cornea can be considered in the calculation, and the line-of-sight vector can be calculated as a vector connecting the correct pupil center and corneal curvature center. In contrast, the eyeball model fitting method is unable to deal with corneal refraction since only the apparent pupil center is obtained as the information relating to the cornea, where the line-of-sight vector is calculated as a vector connecting the apparent pupil center and the eyeball center. As shown in FIG. 13, the line-of-sight vectors gcr and geb do not exactly coincide. In addition, the angle difference (hereinafter referred to as a line-of-sight error) ρ between two line-of-sight vectors is not constant and varies depending on the position and the orientation of the eyeball. If the line-of-sight vector gcr obtained by the corneal reflection method is correct, the large line-of-sight error ρ means deterioration of the line-of-sight estimation accuracy of the eyeball model fitting method.

Therefore, in the embodiment disclosed here, coordinates of the corneal reflection image are estimated from a result of observation of the pupil center. The result is obtained by using an image capturing unit in which it is determined that the camera and the illumination are coaxial, an eyeball center estimation technique, a three-dimensional eyeball model, and a technique of correcting the optical axis vector. The pupil center coordinates are estimated from the result of observation of the corneal reflection image. Since the configuration is implemented by software, no additional hardware is required.

Configuration of Line-of-Sight Measurement Device

Figure 1:
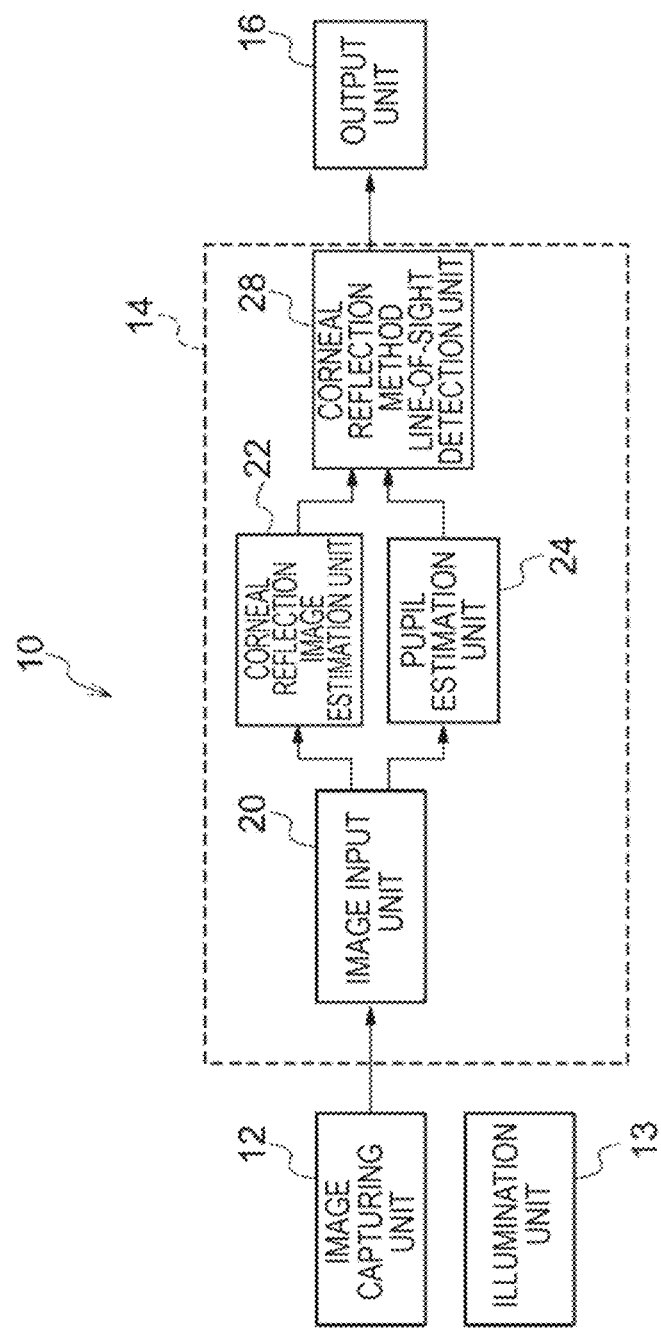
FIG. 1 is a block diagram showing a configuration of a line-of-sight measurement device according to an embodiment disclosed here.

As shown in FIG. 1, the line-of-sight measurement device 10 according to the embodiment disclosed here includes: an image capturing unit 12 including a CCD camera or the like that captures an image including a subject's face as a target; an illumination unit 13 that illuminates light on the subject's eyes; a computer 14 that performs image processing; and an output unit 16 that includes a CRT or the like.

Figure 2:
FIG. 2 is a diagram showing an arrangement of an illumination unit and an image capturing unit.
Figure 3:
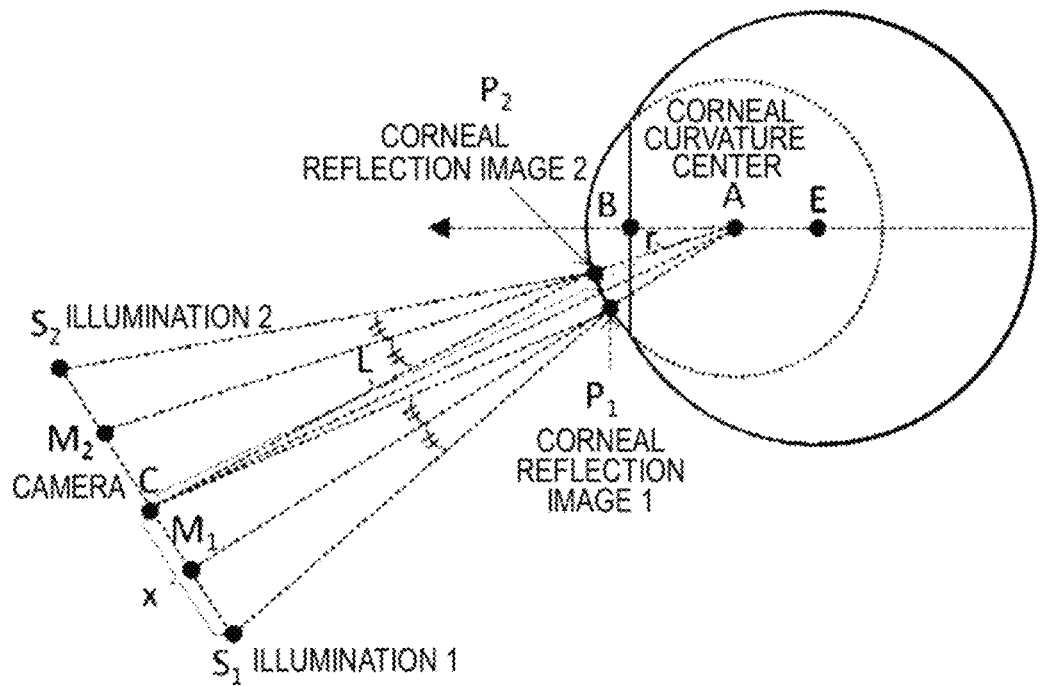
FIG. 3 is a diagram showing a positional relationship between an illumination unit, an image capturing unit, and eyes.

The image capturing unit 12 is one camera, and the illumination unit 13 is, for example, one near infrared LED. In the present embodiment, the imaging direction of the image capturing unit 12 and the illumination direction of the illumination unit 13 are not coaxial, but are arranged such that it is determined that the directions are coaxial (FIG. 2). Specifically, the arrangement satisfies the constraint condition shown in Expression (1) (FIG. 3). It should be noted that two near-infrared LEDs may be arranged on both the left side and the right side of the camera after satisfying Expression (1).

$$x < \frac{L}{f}\frac{r+L}{r} \tag{1}$$

Here, L is the distance between the image capturing unit 12 and the intersection between the cornea and the straight line from the image capturing unit 12 toward the corneal curvature center, r is the radius of corneal curvature, and f is the focal length in units of pixels of the image capturing unit 12.

The computer 14 includes a CPU, a ROM that stores a program for a line-of-sight measurement processing routine to be described later, a RAM that stores data and the like, and a bus that connects these. The computer 14 will be described with function blocks divided for respective units for implementing functions determined on the basis of hardware and software. As shown in FIG. 1, the computer 14 includes an image input unit 20, a corneal reflection image estimation unit 22, a pupil estimation unit 24, and a corneal reflection method line-of-sight detection unit 28. The image input unit 20 inputs a face image as a grayscale image which is output from the image capturing unit 12. The corneal reflection image estimation unit 22 estimates a time series of image coordinates of a corneal reflection image from a time series of a face image which is an output of the image input unit 20. The pupil estimation unit 24 estimates the time series of the image coordinates of the pupil center, from the time series of the face image which is an output of the image input unit 20. The corneal reflection method line-of-sight detection unit 28 calculates a line-of-sight vector in the camera coordinate system using a corneal reflection method (refer to FIG. 11) from the time series of the image coordinates of the corneal reflection image and the time series of the image coordinates of the pupil center.

The image input unit 20 includes, for example, an A/D converter, an image memory that stores image data for one screen, and the like.

Figure 4:
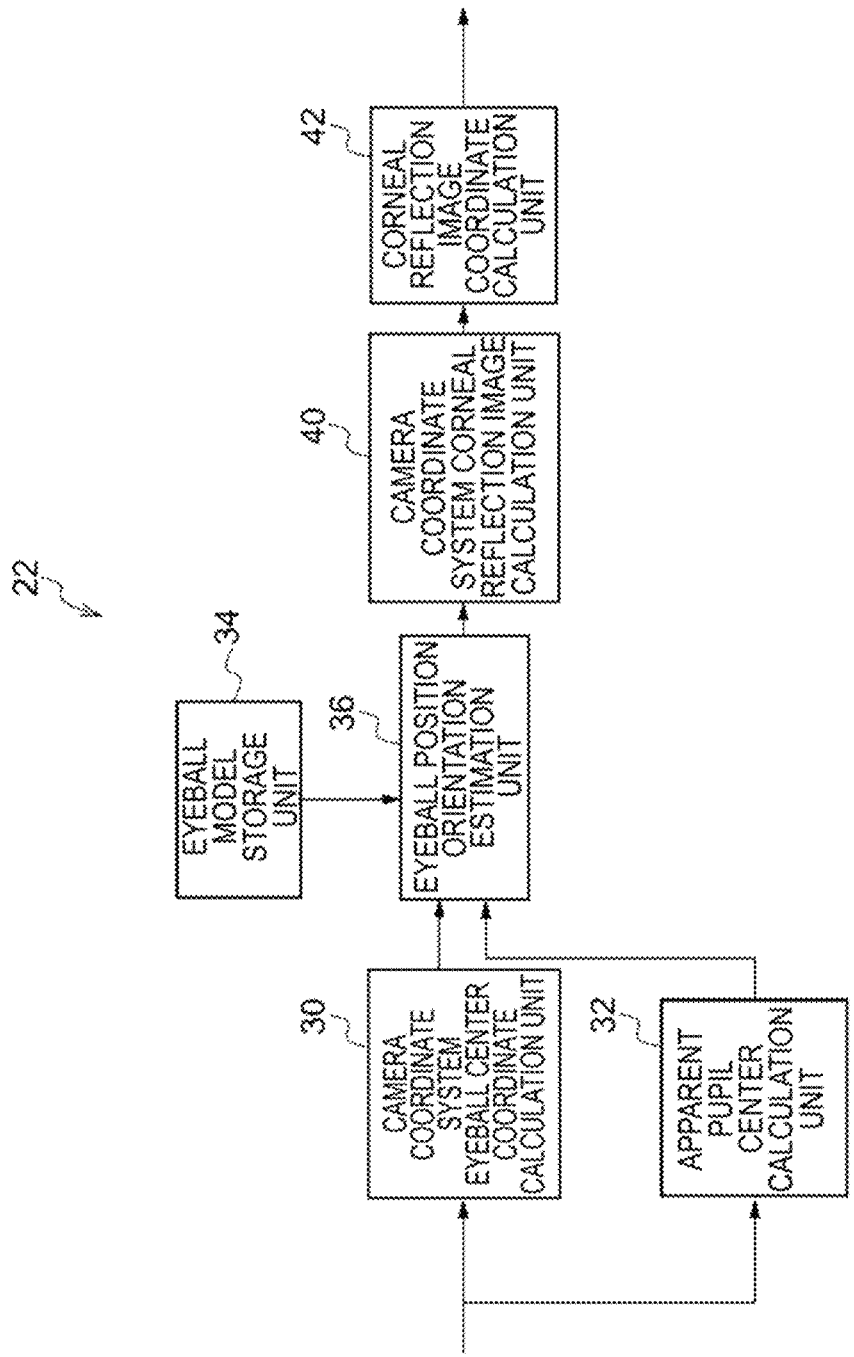
FIG. 4 is a block diagram showing a configuration of a corneal reflection image estimation unit of the line-of-sight measurement device according to the embodiment disclosed here.

As shown in FIG. 4, the corneal reflection image estimation unit 22 includes a camera coordinate system eyeball center coordinate calculation unit 30, an apparent pupil center calculation unit 32, an eyeball model storage unit 34, an eyeball position orientation estimation unit 36, a camera coordinate system corneal reflection image calculation unit 40, and a corneal reflection image coordinate calculation unit 42.

The camera coordinate system eyeball center coordinate calculation unit 30 estimates the three-dimensional coordinates of the eyeball center in the camera coordinate system shown in FIG. 5 from the face image as follows.

Figure 5:
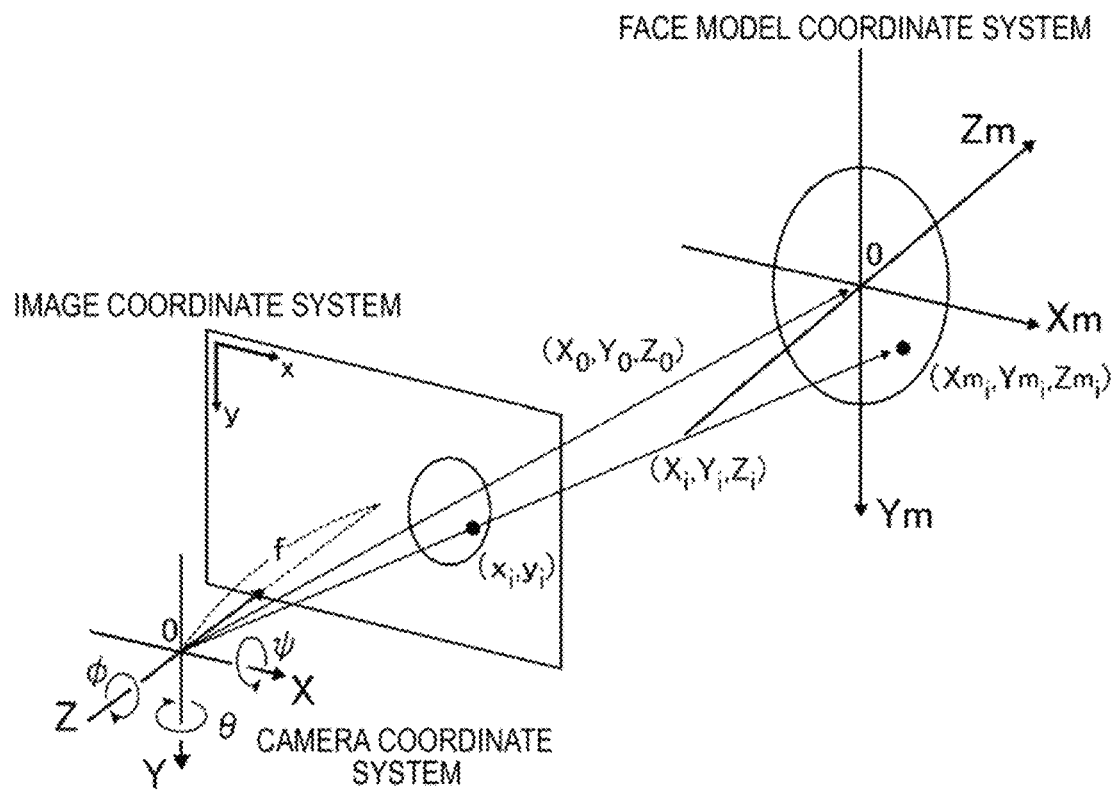
FIG. 5 is a diagram for explaining various coordinate systems.
Figure 6:
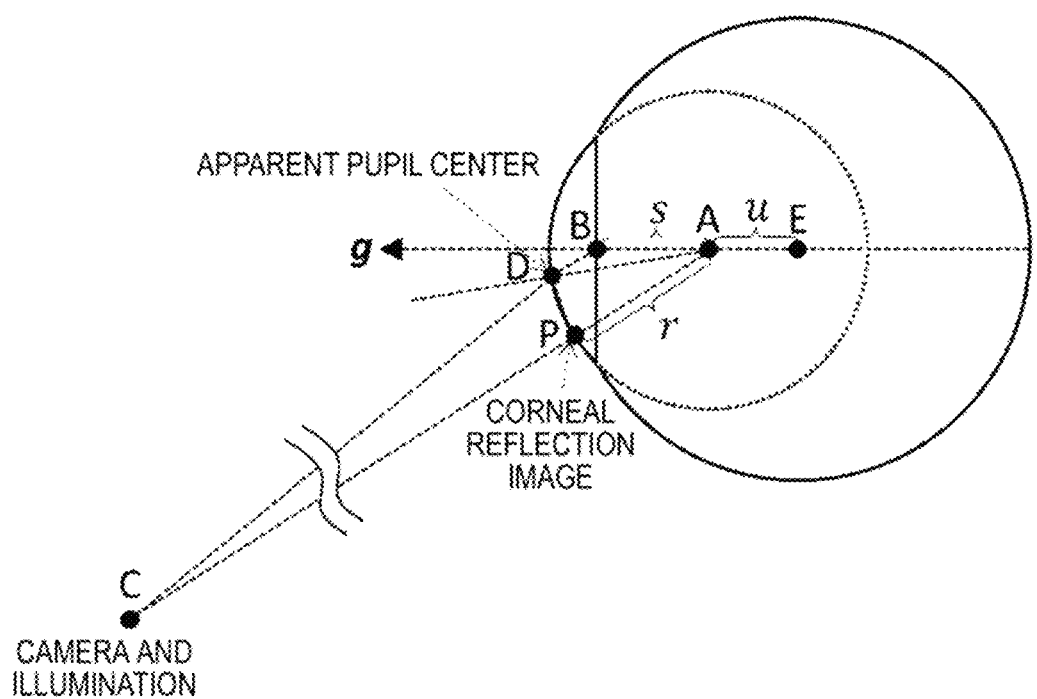
FIG. 6 is a diagram showing a positional relationship between a three-dimensional eyeball model and an image capturing unit.

First, the following three-dimensional coordinates of the eyeball center (point E) in the face model coordinate system shown in FIG. 5 are obtained in advance (refer to FIG. 6).

$$\vec{CE} = e_m$$

For example, the line of sight is calculated using the corneal curvature center and the pupil center calculated from the corneal reflection image of the face image, and the three-dimensional coordinates of the eyeball center in the eyeball model coordinate system are estimated using the calculated line of sight.

Then, the position orientation (rotation translation vector) of the face model coordinate system in the camera coordinate system is obtained.

For example, the current rotation matrix R and translation vector t of the face model coordinate system with respect to the camera coordinate system are obtained by fitting the face model to the current face image.

Then, the three-dimensional coordinates of the eyeball center in the face model coordinate system are converted into the three-dimensional coordinates of the eyeball center in the camera coordinate system, on the basis of the obtained rotation translation vector.

Specifically, the current three-dimensional coordinates e of the eyeball center in the camera coordinate system are calculated in accordance with the following expression.

$$e = Re_m + t \quad (2)$$

As will be described below, the apparent pupil center calculation unit 32 estimates the three-dimensional coordinates of the apparent pupil center in the camera coordinate system from the pupil center position of the eye on the face image.

First, the pupil center is detected from the face image, and the pupil center coordinates in the image coordinate system shown in FIG. 5 are obtained.

Specifically, the pupil center is detected using a known technique in the past, and the following pupil center coordinates in the image coordinate system are obtained.

$$D = (D_x, D_y)$$

Then, the three-dimensional coordinates in a camera coordinate system are estimated from the image coordinates of the pupil center.

Specifically, the Z coordinate of the pupil center in the camera coordinate system is obtained by some distance measurement unit and is set as dz. The coordinates of the image center are set as (xc, yc). The following three-dimensional coordinates of the pupil center in the camera coordinate system are obtained.

$$d = (d_x, d_y, d_z)$$

The three-dimensional coordinates are represented as follows if the focal length expressed in pixel units is f.

$$f = \left( \frac{(D_x - x_c) d_z}{f}, \frac{(D_y - y_c) d_z}{f}, d_z \right) \quad (3)$$

The eyeball model storage unit 34 stores an eyeball model, which is formed of two spheres, and parameters thereof. Specifically, the eyeball model storage unit 34 stores a radius of corneal curvature r, a distance u between the eyeball center E and the corneal curvature center A, a distances between the corneal curvature center A and the true pupil center B, and a ratio (n1/n2) of a refractive index n1 of the atmosphere to a refractive index n2 of the aqueous humor. The distance s between the corneal curvature center A and the true pupil center B and the ratio (n1/n2) of the refractive index n1 of the atmosphere to the refractive index n2 of the aqueous humor are parameters used in a case of calculating the line-of-sight vector in the camera coordinate system through the corneal reflection method using the corneal reflection method line-of-sight detection unit 28.

As will be described below, the eyeball position orientation estimation unit 36 calculates a three-dimensional optical axis vector toward the three-dimensional position of the pupil center from the three-dimensional position of the eyeball center in the camera coordinate system, on the basis of the three-dimensional coordinates of the eyeball center in the camera coordinate system and the three-dimensional coordinates of the apparent pupil center in the camera coordinate system.

First, an angle correction amount is estimated from the fact that the imaging direction of the image capturing unit 12 and the illumination direction of the illumination unit 13 are arranged such that it is determined that the directions are coaxial, and from a corner CED shown in FIG. 6.

Specifically, the vector from the eyeball center E to the apparent pupil center is represented as follows.

$$\vec{ED} = g_{eb}$$

Then, the following expression is obtained.

$$g_{eb} = d - e = \begin{pmatrix} \frac{(D_x - x_c) z}{f} - e_x \\ \frac{(D_y - y_c) d_z}{f} - e_y \\ d_z - e_z \end{pmatrix} \quad (4)$$

The corner CED is formed by a line segment connecting the three-dimensional coordinates of the apparent pupil center in the camera coordinate system and the three-dimensional coordinates of the eyeball center in the camera coordinate system, and a line segment connecting the three-dimensional coordinates of the eyeball center in the camera coordinate system and the three-dimensional coordinates of the imaging unit. The angle ω of the corner CED is represented as follows.

$$<CED = \omega$$

The angle ω is calculated in accordance with the following expression.

$$\omega = \arccos\left( \frac{g_{eb} \cdot (-e)}{\|g_{eb}\| \|-e\|} \right) = \quad (5)$$

$$\arccos \left( \frac{-\left( \frac{(D_x - x_c) d_z}{f} - e_x \right) e_x - \left( \frac{(D_y - y_c) d_z}{f} - e_y \right) e_y - (d_z - e_z) e_z}{\sqrt{\left( \frac{(D_x - x_c) d_z}{f} - e_x \right)^2 + \left( \frac{(D_y - y_c) d_z}{f} - e_y \right)^2 + (d_z - e_z)^2} \sqrt{e_x^2 + e_y^2 + e_z^2}} \right)$$

Then, a relationship between the angle of the corner CED and the angle difference p between the line-of-sight vector gcr obtained by the corneal reflection method and the line-of-sight vector geb obtained by the eyeball model fitting method is obtained in advance. By using the relationship, the angle difference ρ corresponding to the angle of the corner CED is calculated as a correction amount ρ.

Then, a three-dimensional optical axis vector g toward the three-dimensional coordinates of the pupil center from the three-dimensional coordinates of the eyeball center in the camera coordinate system is calculated by the following expression, on the basis of the three-dimensional coordinates e of the eyeball center in the camera coordinate system, the vector geb from the eyeball center E to the apparent pupil center, and the angle correction amount ρ.

$$g = g_{eb}\cos\rho + \left(\frac{-g_{eb} \times e}{\|g_{eb}\| \times e\|}\right) \times g_{eb}\sin\rho + \left(\frac{-g_{eb} \times e}{\|g_{eb} \times e\|}\right)\left(\frac{-g_{eb} \times e}{\|g_{eb} \times e\|} \cdot g_{eb}\right)(1 - \cos\rho) \quad (6)$$

Thus, the optical axis vector is determined from the correction amount and the three-dimensional coordinates of the eyeball center, and is combined with the three-dimensional coordinates of the eyeball center. Then, the position and the orientation of the eyeball model can be estimated.

As will be described below, the camera coordinate system corneal reflection image calculation unit 40 obtains the three-dimensional coordinates of the corneal reflection image in the camera coordinate system, on the basis of the three-dimensional coordinates of the eyeball center in the camera coordinate system, the optical axis vector, and a predetermined three-dimensional eyeball model.

First, the three-dimensional coordinate a of the corneal curvature center A in the camera coordinate system is estimated in accordance with the following expression, by using the three-dimensional coordinates e of the eyeball center in the camera coordinate system, the optical axis vector g, and the distance u between the eyeball center E and the corneal curvature center A stored in the eyeball model storage unit 34.

$$a = e + u\frac{g}{\|g\|} \quad (7)$$

Then, a point on the vector CA where the distance from the corneal curvature center A becomes equal to r is obtained.

Specifically, a three-dimensional vector of the corneal reflection image P is represented as follows.

$$p=(p_x, p_y, p_z)$$

Then, the point P becomes a point which is closer to the point C by a length r than the point A on the straight line CA. Therefore, p can be obtained by Expression (8).

$$p = \frac{a}{\|a\|}(\|a\| - r) \quad (8)$$

The corneal reflection image coordinate calculation unit 42 estimates the image coordinates of the corneal reflection image on the face image from the three-dimensional coordinates of the corneal reflection image in the camera coordinate system, as described below.

First, the three-dimensional coordinates of the corneal reflection image in the camera coordinate system are two-dimensionally projected using the camera parameters.

Specifically, if the focal length expressed in pixel units is f and the coordinates of the image center are (xc, yc), the image coordinates (Px, Py) of the corneal reflection image are as follows.

$$P_x = f\frac{p_x}{p_z} + x_c \quad (9)$$

$$P_y = f\frac{p_y}{p_z} + y_c \quad (10)$$

Through the processing of each unit described above, the image coordinates of the corneal reflection image can be estimated from the observed value of the pupil center.

Figure 7:
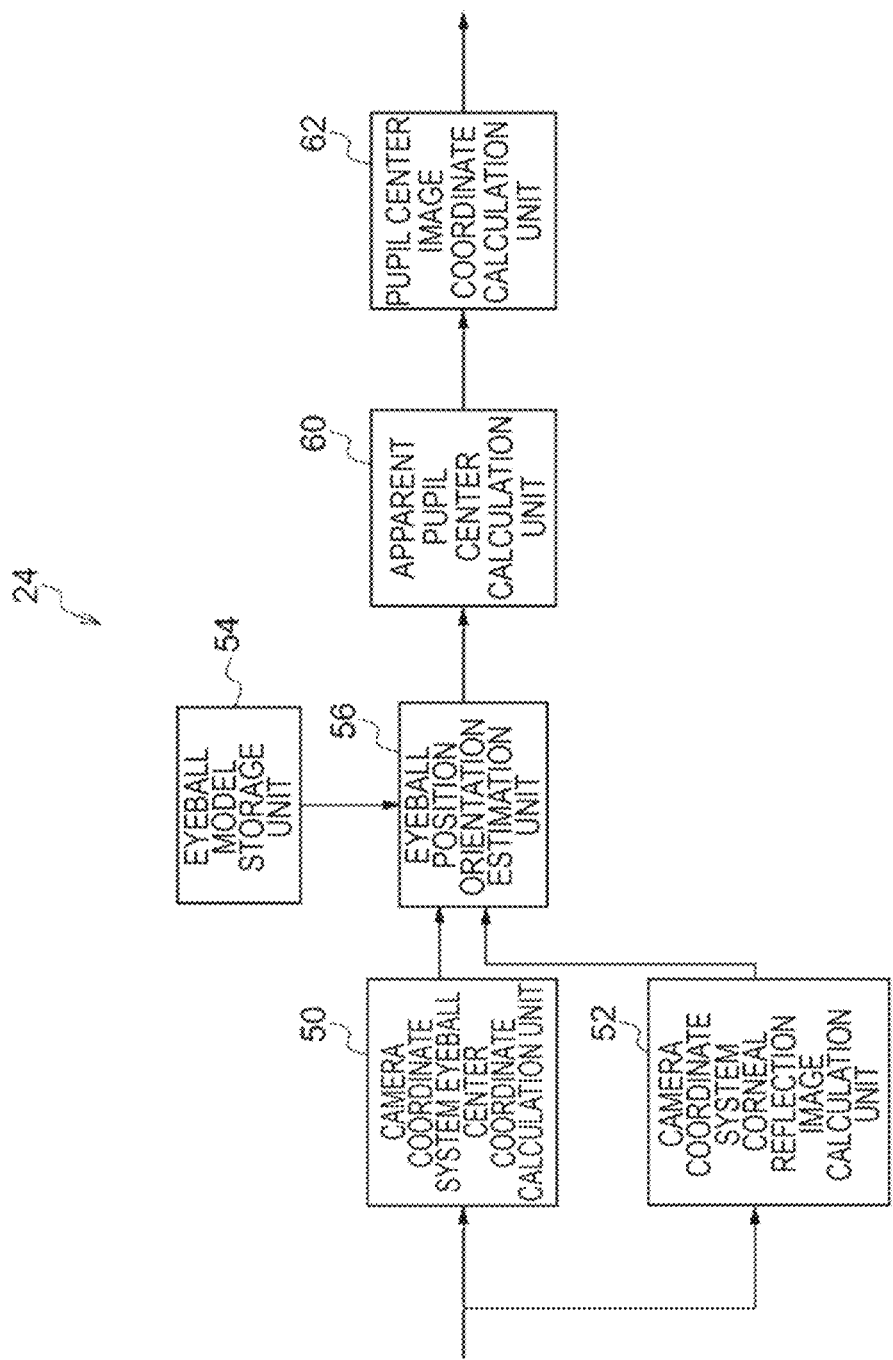
FIG. 7 is a block diagram showing a configuration of a pupil estimation unit of the line-of-sight measurement device according to the embodiment disclosed here.

As shown in FIG. 7, the pupil estimation unit 24 includes a camera coordinate system eyeball center coordinate calculation unit 50, a camera coordinate system corneal reflection image calculation unit 52, an eyeball model storage unit 54, an eyeball position orientation estimation unit 56, an apparent pupil center calculation unit 60, and a pupil center image coordinate calculation unit 62.

Similarly to the camera coordinate system eyeball center coordinate calculation unit 30, the camera coordinate system eyeball center coordinate calculation unit 50 estimates the three-dimensional coordinates of the eyeball center in the camera coordinate system from the face image.

The camera coordinate system corneal reflection image calculation unit 52 estimates the three-dimensional coordinates of the corneal reflection image in the camera coordinate system from the position of the eye corneal reflection image on the face image.

First, using a known technique in the past, a corneal reflection image is detected from the face image, and the following coordinates of the corneal reflection image in the image coordinates are obtained.

$$P=(P_x, P_y)$$

Then, the three-dimensional coordinates of the corneal reflection image in the camera coordinate system are estimated from the image coordinates of the corneal reflection image.

Specifically, the Z coordinate of the corneal reflection image coordinates in the camera coordinate system is obtained by some distance measurement unit and is set as pz. The coordinates of the image center are set as (xc, yc). The following three-dimensional coordinates of the corneal reflection image in the camera coordinate system are obtained.

$$p=(p_x, p_y, p_z)$$

The three-dimensional coordinates are represented as follows if the focal length expressed in pixel units is f.

$$p = \left(\frac{(P_x - x_c)p_z}{f}, \frac{(P_y - y_c)p_z}{f}, p_z\right) \quad (11)$$

Similarly to the eyeball model storage unit 34, the eyeball model storage unit 54 stores a radius of corneal curvature r, a distance u between the eyeball center E and the corneal curvature center A, a distance s between the corneal curvature center A and the true pupil center B, and a ratio (n1/n2) of a refractive index n1 of the atmosphere to a refractive index n2 of the aqueous humor. The distance s between the corneal curvature center A and the true pupil center B and the ratio (n1/n2) of the refractive index n1 of the atmosphere to the refractive index n2 of the aqueous humor are parameters used in a case of calculating the line-of-sight vector in the camera coordinate system through the corneal reflection method using the corneal reflection line-of-sight detection unit 28.

As will be described below, the eyeball position orientation estimation unit 56 calculates a three-dimensional optical axis vector toward the three-dimensional position of the corneal curvature center from the three-dimensional position of the eyeball center in the camera coordinate system, on the basis of the three-dimensional coordinates of the eyeball center in the camera coordinate system and the three-dimensional coordinates of the corneal reflection image in the camera coordinate system.

First, the three-dimensional coordinates of the corneal curvature center A in the camera coordinate system are estimated using the fact that it is determined that the imaging direction of the image capturing unit 12 and the illumination direction of the illumination unit 13 are arranged to be coaxial, the three-dimensional coordinates p of the corneal reflection image in the camera coordinate system, and the radius of corneal curvature r.

Specifically, if a three-dimensional vector of the corneal curvature center A is a, a is obtained by extending the straight line CP on the P side by the length r, and is represented by the following expression.

$$a = \frac{p}{\|p\|}(\|p\| + r) \qquad (12)$$

Then, an optical axis vector is obtained from the three-dimensional coordinates of the corneal curvature center A in the camera coordinate system and the three-dimensional coordinates of the eyeball center in the camera coordinate system.

Specifically, the optical axis vector g is a vector toward the corneal curvature center A in the camera coordinate system from the eyeball center E in the camera coordinate system, and is thus calculated in accordance with the following expression.

$$g = a - e \qquad (13)$$

As described above, the position and the orientation of the eyeball model can be estimated by determining the optical axis vector and combining the optical axis vector with the estimated values of the eyeball center coordinates.

As will be described below, the apparent pupil center calculation unit 60 obtains the three-dimensional coordinates of the apparent pupil center in the camera coordinate system, on the basis of the three-dimensional coordinates of the eyeball center in the camera coordinate system, the optical axis vector, and a predetermined three-dimensional eyeball model.

First, on the basis of the optical axis vector g and the three-dimensional coordinates e of the eyeball center in the camera coordinate system, an angle of a corner CEA is calculated. The corner CEA is formed by a line segment EA and a line segment EC. The line segment EA connects the three-dimensional coordinates E of the eyeball center in the camera coordinate system and the three-dimensional coordinates A of the corneal curvature center of the camera coordinate system. The line segment EC connects the three-dimensional coordinates E of the eyeball center in the camera coordinate system and the three-dimensional coordinates C of the image capturing unit 12.

Specifically, if the angle of the corner CED is ω, the angle of the corner DEA is ρ, and the angle of the corner CEA is ώ, the following expression is obtained.

$$\acute{\omega} = \omega + \rho \qquad (14)$$

Accordingly, through the inner product calculation, ώ is obtained by the following expression.

$$\acute{\omega} = \arccos \frac{(-e) \cdot g}{\|-e\|\|g\|} \qquad (15)$$

Then, a predetermined angle correction amount corresponding to the calculated angle of the corner CEA is acquired.

Specifically, a relationship between the angle of the corner CEA and the angle difference ρ between the line-of-sight vector gcr obtained by the corneal reflection method and the line-of-sight vector geb obtained by the eyeball model fitting method is obtained in advance. By using the relationship, the angle difference p corresponding to the angle of the corner CEA is calculated as a correction amount ρ.

Then, a vector geb connecting the three-dimensional coordinates E of the eyeball center in the camera coordinate system and the three-dimensional coordinates A of the corneal curvature center in the camera coordinate system is calculated by the following expression, on the basis of the three-dimensional coordinates e of the eyeball center in the camera coordinate system, the optical axis vector g, and the angle correction amount ρ.

$$g_{eb} \approx g\cos(-\rho) + \left(\frac{-g \times e}{\|g \times e\|}\right) \times g\sin(-\rho) + \left(\frac{-g \times e}{\|g \times e\|}\right)\left(\frac{-g \times e}{\|g \times e\|} \cdot g\right)(1 - \cos(-\rho))$$

Then, a point where the distance from the corneal curvature center A becomes equal to r is obtained on a vector geb connecting the three-dimensional coordinates E of the eyeball center in the camera coordinate system and the three-dimensional coordinates A of the corneal curvature center in the camera coordinate system.

Specifically, a distance between E and D is set as x. In the triangle EDA, since AE=u, AD=r, and the angle of the corner DEA=ρ, Expression (17) is established by the cosine theorem. Expression (17), which is a quadratic equation of x, is solved for x, and the larger solution is set as the distance x between E and D.

$$r^2 = x^2 + u^2 - 2xu \cos \rho \qquad (17)$$

A three-dimensional vector of the pupil center D is represented as follows.

$$d = (d_x, d_y, d_z)$$

Then, since D is a point at a distance x from E on the vector geb, d is obtained by Expression (18).

$$d = x\frac{g_{eb}}{\|g_{eb}\|} - e \qquad (18)$$

The pupil center image coordinate calculation unit 62 estimates the image coordinates of the pupil center on the face image from the three-dimensional coordinates of the apparent pupil center in the camera coordinate system.

Specifically, the three-dimensional coordinates of the apparent pupil center in the camera coordinate system are two-dimensionally projected using the camera parameters.

For example, if f is a focal length expressed in units of pixels and the coordinates of the image center are (xc, yc), the image coordinates (Dx, Dy) of the pupil center are as follows.

$$D_x = f \frac{d_x}{d_z} + x_c \quad (19)$$

$$D_y = f \frac{d_y}{d_z} + y_c \quad (20)$$

Through the processing of each unit described above, the image coordinates of the pupil center can be estimated from the observed value of the corneal reflection image.

The corneal reflection method line-of-sight detection unit 28 obtains a line-of-sight vector by the corneal reflection method on the basis of the image coordinates of the corneal reflection image and the image coordinates of the pupil center, and outputs the line-of-sight vector by the output unit 16.

At this time, by comparing the estimated value of the corneal reflection image with the observed value of the detected corneal reflection image, it is determined whether the observed value of the corneal reflection image is correct. In addition, by comparing the estimated value of the pupil center with the observed value of the detected pupil center, it is determined whether the observed value of the pupil center is correct. Then, the line-of-sight vector is obtained by the corneal reflection method using the observed value of the corneal reflection image determined to be correct and the observed value of the pupil center.

Operation of Line-of-Sight Measurement Device

Next, the operation of the line-of-sight measurement device 10 will be described. First, if the illumination unit 13 illuminates the near-infrared light on the subject's eyes, the image capturing unit 12 continuously captures the face image of the subject.

Figure 8:
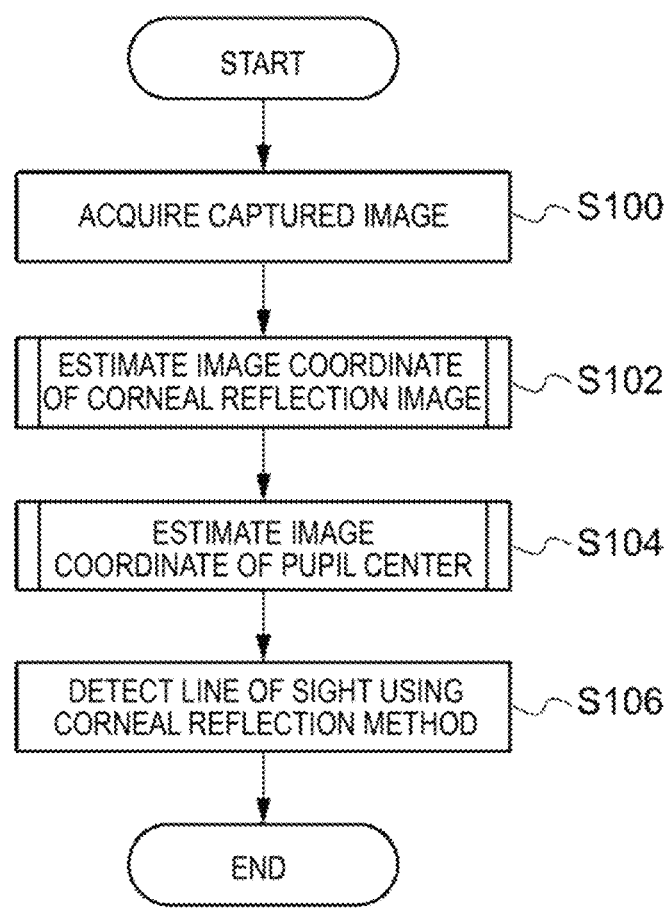
FIG. 8 is a flowchart showing the contents of a line-of-sight measurement processing routine in the line-of-sight measurement device according to the embodiment disclosed here.

Then, the computer 14 executes a line-of-sight measurement processing routine shown in FIG. 8 for each captured face image.

First, in step S100, the face image captured by the image capturing unit 12 is acquired.

In step S102, the image coordinates of the corneal reflection image are estimated from the face image.

In step S104, the image coordinates of the pupil center are estimated from the face image.

In step S106, a line-of-sight vector is obtained by the corneal reflection method on the basis of the image coordinates of the corneal reflection image and the image coordinates of the pupil center, and is output by the output unit 16, and the line-of-sight measurement processing routine ends.

Figure 9:
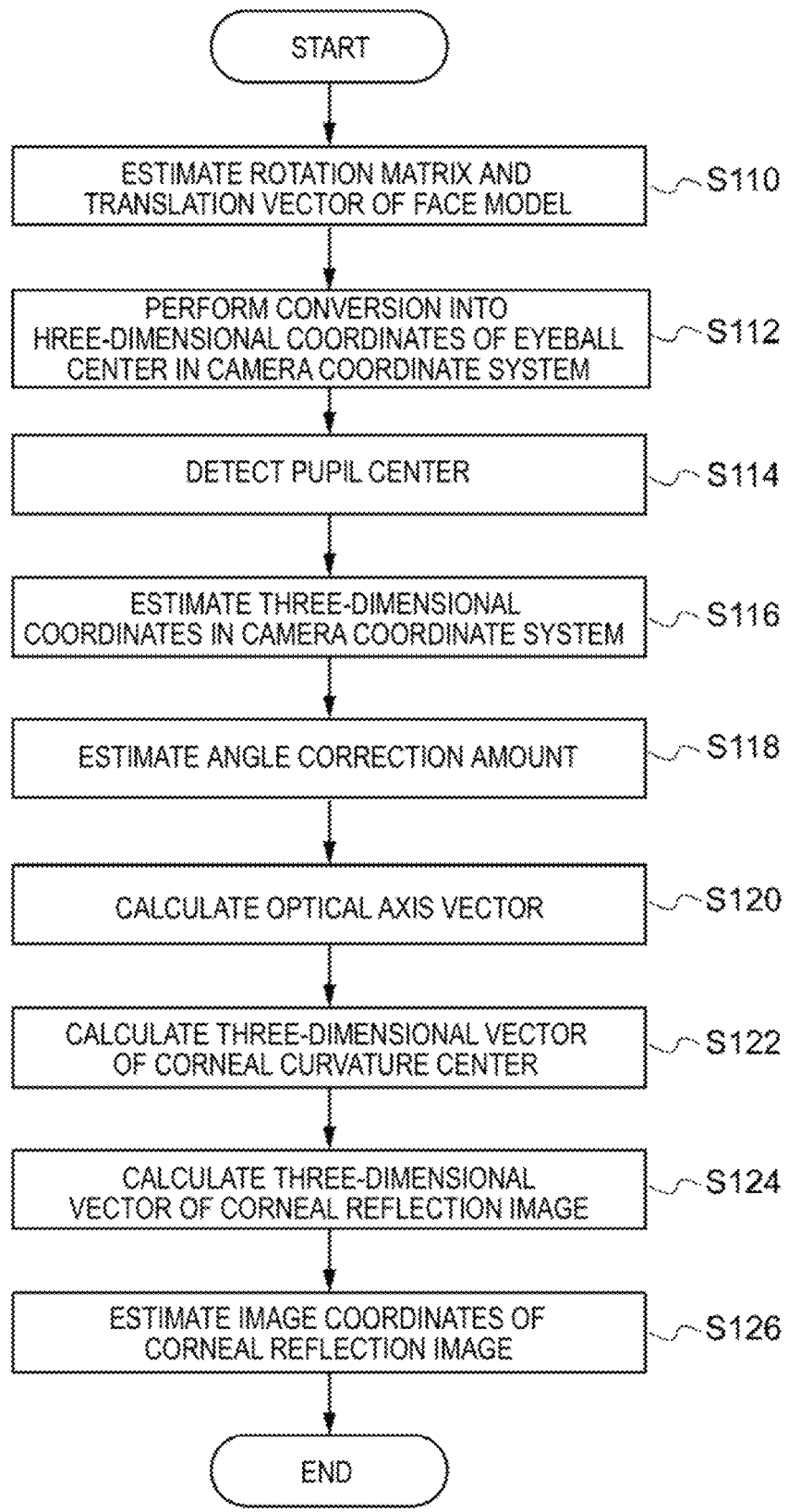
FIG. 9 is a flowchart showing the contents of a corneal reflection image estimation processing routine in the line-of-sight measurement device according to the embodiment disclosed here.

Step S102 is realized through the corneal reflection image estimation processing routine shown in FIG. 9.

First, in step S110, the current rotation matrix R and translation vector t of the face model coordinate system with respect to the camera coordinate system are obtained by fitting the face model to the current face image.

In step S112, the three-dimensional coordinates of the eyeball center in the face model coordinate system are converted into the three-dimensional coordinates of the eyeball center in the camera coordinate system, on the basis of the obtained rotation translation vector.

In step S114, the pupil center is detected from the face image, and the pupil center coordinates in the image coordinate system are obtained.

In step S116, the three-dimensional coordinates in the camera coordinate system are estimated from the image coordinates of the pupil center.

In step S118, an angle correction amount is estimated from the angle of the corner CED and the fact that the imaging direction of the image capturing unit 12 and the illumination direction of the illumination unit 13 are arranged such that it is determined that the directions are coaxial. The angle of the corner CED is formed by the line segment connecting the three-dimensional coordinates of the apparent pupil center in the camera coordinate system and the three-dimensional coordinates of the eyeball center in the camera coordinate system and the line segment connecting the three-dimensional coordinates of the eyeball center in the camera coordinate system and the three-dimensional coordinates of the imaging unit.

In step S120, the three-dimensional optical axis vector g toward the three-dimensional position of the pupil center from the three-dimensional position of the eyeball center in the camera coordinate system is calculated on the basis of the angle ω of the corner CED, the three-dimensional coordinates e of the eyeball center in the camera coordinate system, and the angle correction amount.

In step S122, the three-dimensional coordinates a of the corneal curvature center A in the camera coordinate system is estimated using the three-dimensional coordinates e of the eyeball center in the camera coordinate system, the optical axis vector g, and the distance u between the eyeball center E and the corneal curvature center A stored in the eyeball model storage unit 34.

In step S124, a point where the distance from the corneal curvature center A becomes equal to r is obtained on the vector CA, and a three-dimensional vector of the corneal reflection image P is estimated.

In step S126, the image coordinates of the corneal reflection image on the face image are estimated from the three-dimensional coordinates of the corneal reflection image in the camera coordinate system.

Figure 10:
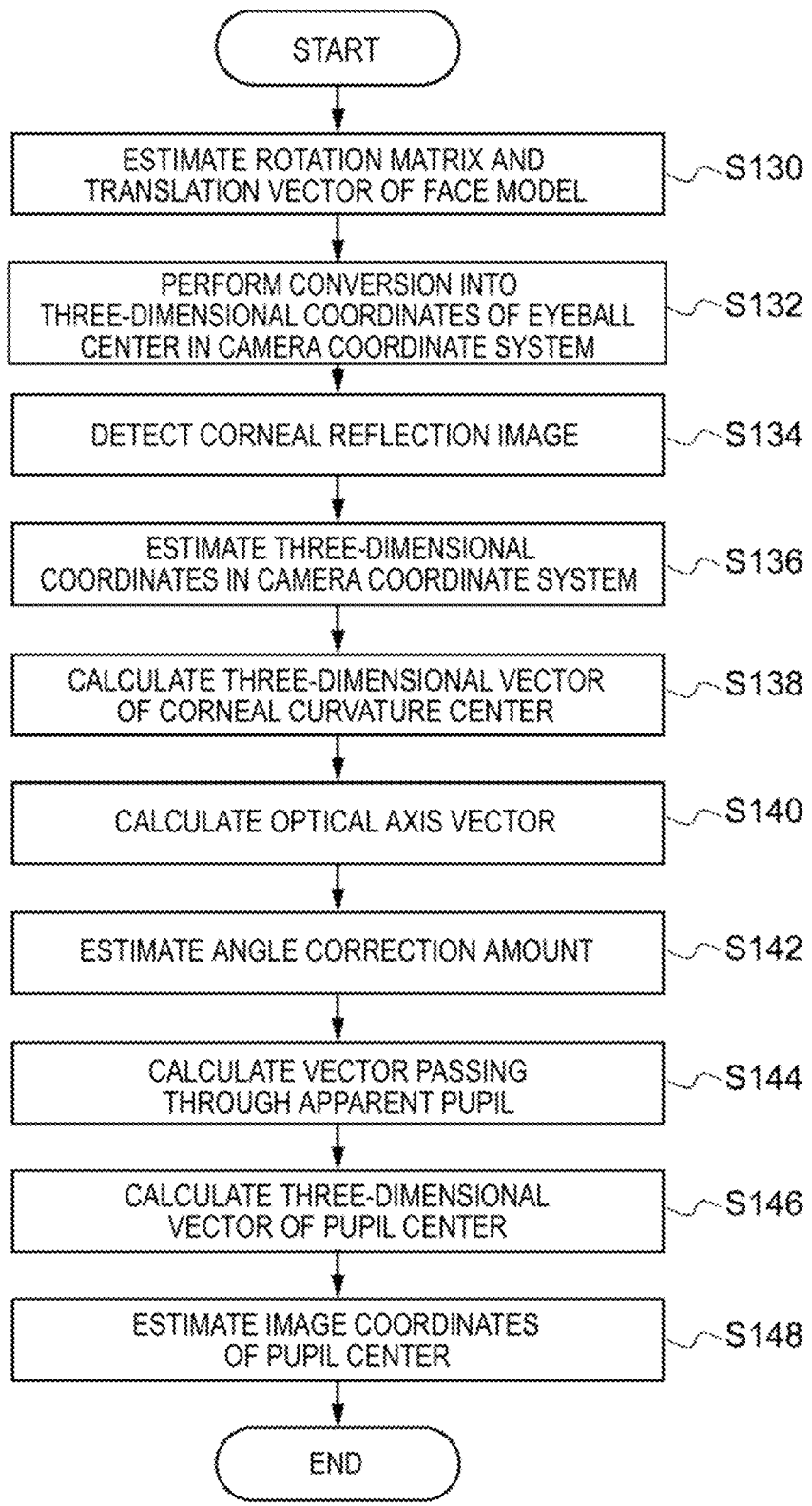
FIG. 10 is a flowchart showing the contents of a pupil estimation processing routine in the line-of-sight measurement device according to the embodiment disclosed here.

Step S104 is realized by the pupil center estimation processing routine shown in FIG. 10.

First, in step S130, the current rotation matrix R and translation vector t of the face model coordinate system with respect to the camera coordinate system are obtained by fitting the face model to the current face image.

In step S132, the three-dimensional coordinates of the eyeball center in the face model coordinate system are converted into the three-dimensional coordinates of the eyeball center in the camera coordinate system, on the basis of the obtained rotation translation vector.

In step S134, a corneal reflection image is detected from the face image, and the coordinates of the corneal reflection image in the image coordinates are obtained.

In step S136, the three-dimensional coordinates of the corneal reflection image in the camera coordinate system are estimated from the image coordinates of the corneal reflection image.

In step S138, the three-dimensional coordinates of the corneal curvature center A in the camera coordinate system are estimated using the fact that it is determined that the imaging direction of the image capturing unit 12 and the illumination direction of the illumination unit 13 are arranged to be coaxial, the three-dimensional coordinates p of the corneal reflection image in the camera coordinate system, and the radius of corneal curvature r.

In step S140, an optical axis vector is obtained from the three-dimensional coordinates of the corneal curvature center A in the camera coordinate system and the three-dimensional coordinates of the eyeball center in the camera coordinate system.

In step S142, on the basis of the optical axis vector g and the three-dimensional coordinates e of the eyeball center in the camera coordinate system, an angle of a corner CEA is calculated. The corner CEA is formed by a line segment EA and a line segment EC. The line segment EA connects the three-dimensional coordinates E of the eyeball center in the camera coordinate system and the three-dimensional coordinates A of the corneal curvature center of the camera coordinate system. The line segment EC connects the three-dimensional coordinates E of the eyeball center in the camera coordinate system and the three-dimensional coordinates C of the image capturing unit 12. Thereby, a predetermined angle correction amount corresponding to the calculated angle of the corner CEA is acquired.

In step S144, a vector geb connecting the three-dimensional coordinates E of the eyeball center in the camera coordinate system and the three-dimensional coordinates A of the corneal curvature center in the camera coordinate system is calculated, on the basis of the three-dimensional coordinates e of the eyeball center in the camera coordinate system, the optical axis vector g, and the angle correction amount ρ.

In step S146, a point where the distance from the corneal curvature center A becomes equal to r is obtained on a vector geb connecting the three-dimensional coordinates E of the eyeball center in the camera coordinate system and the three-dimensional coordinates A of the corneal curvature center in the camera coordinate system. The point is set as the three-dimensional coordinates of the apparent pupil center in the camera coordinate system.

In step S148, the image coordinates of the pupil center on the face image are estimated from the three-dimensional coordinates of the apparent pupil center in the camera coordinate system.

As described above, by using the line-of-sight measurement device according to the embodiment disclosed here, image coordinates of the corneal reflection image on the face image can be obtained with high accuracy from the eye pupil center position on the face image in order to perform line-of-sight measurement with a simple configuration. The image coordinates of the pupil center on the face image can be obtained with high accuracy from the position of the corneal reflection image of the eye on the face image in order to perform line-of-sight measurement with a simple configuration.

Model-based estimation of the other image coordinates can be performed from one result of observation of two observed values (pupil center and the corneal reflection image) used in the corneal reflection method, by using the image capturing unit in which it is determined that the camera and the illumination are coaxial, an eyeball center estimation technique, a three-dimensional eyeball model, and a technique of correcting the optical axis vector. Thereby, it is possible to determine whether the result of observation is correct by comparing the observed value with the estimated value, and it is possible to increase the reliability of the observation at a low cost.

A line-of-sight measurement device according to a first aspect of this disclosure includes: an imaging unit that images a face of a subject to be observed; a light illumination unit that illuminates light to an eye of the subject to be observed; a camera coordinate system eyeball center coordinate calculation unit that estimates three-dimensional coordinates of an eyeball center in a camera coordinate system, from a face image representing the face imaged by the imaging unit; a pupil center calculation unit that estimates three-dimensional coordinates of an apparent pupil center in the camera coordinate system, from a pupil center position of the eye on the face image; an eyeball position orientation estimation unit that calculates a three-dimensional optical axis vector toward a three-dimensional position of the pupil center from a three-dimensional position of the eyeball center, in the camera coordinate system, on the basis of the three-dimensional coordinates of the eyeball center in the camera coordinate system and the three-dimensional coordinates of the apparent pupil center in the camera coordinate system; a corneal reflection image calculation unit that obtains three-dimensional coordinates of a corneal reflection image in the camera coordinate system, on the basis of the three-dimensional coordinates of the eyeball center in the camera coordinate system, the optical axis vector, and a predetermined three-dimensional eyeball model; and an image coordinate calculation unit that estimates image coordinates of a corneal reflection image on the face image, from the three-dimensional coordinates of the corneal reflection image in the camera coordinate system.

According to the first aspect of this disclosure, the image coordinates of the corneal reflection image on the face image can be obtained with high accuracy from the pupil center position of the eye on the face image in order to perform line-of-sight measurement with a simple configuration.

In the line-of-sight measurement device according to the first aspect, a positional relationship between the imaging unit and the light illumination unit, a positional relationship between the imaging unit and the eye, and parameters relating to the imaging unit may satisfy a predetermined constraint for determining that an imaging direction of the imaging unit and a light illumination direction of the light illumination unit are coaxial.

In the line-of-sight measurement device according to the first aspect, the eyeball position orientation estimation unit may calculate an angle formed by a line segment connecting the three-dimensional coordinates of the apparent pupil center in the camera coordinate system and the three-dimensional coordinates of the eyeball center in the camera coordinate system and a line segment connecting the three-dimensional coordinates of the eyeball center in the camera coordinate system and three-dimensional coordinates of the imaging unit, acquire a predetermined angle correction amount corresponding to the angle, and calculate the three-dimensional optical axis vector toward the three-dimensional position of the pupil center from the three-dimensional position of the eyeball center in the camera coordinate system, on the basis of a vector connecting the three-dimensional coordinates of the eyeball center in the camera coordinate system and the three-dimensional coordinates of the apparent pupil center in the camera coordinate system, the acquired angle correction amount, the calculated angle, and the three-dimensional coordinates of the eyeball center in the camera coordinate system.

A line-of-sight measurement device according to a second aspect of this disclosure includes: an imaging unit that images a face of a subject to be observed; a light illumination unit that illuminates light to an eye of the subject to be observed; a camera coordinate system eyeball center coordinate calculation unit that estimates three-dimensional coordinates of an eyeball center in a camera coordinate system, from a face image representing the face imaged by the imaging unit; a corneal reflection image calculation unit that estimates three-dimensional coordinates of a corneal reflection image in the camera coordinate system, from a position of the corneal reflection image of the eye on the face image; an eyeball position orientation estimation unit that calculates a three-dimensional optical axis vector toward a three-dimensional position of a corneal curvature center from a three-dimensional position of the eyeball center, in the camera coordinate system, on the basis of the three-dimensional coordinates of the eyeball center in the camera coordinate system and the three-dimensional coordinates of the corneal reflection image in the camera coordinate system; a pupil center calculation unit that obtains three-dimensional coordinates of an apparent pupil center in the camera coordinate system, on the basis of the three-dimensional coordinates of the eyeball center in the camera coordinate system, the optical axis vector, and a predetermined three-dimensional eyeball model; and an image coordinate calculation unit that estimates image coordinates of a pupil center on the face image, from the three-dimensional coordinates of the apparent pupil center in the camera coordinate system.

According to the second aspect, the image coordinates of the pupil center on the face image can be obtained with high accuracy from the position of the corneal reflection image of the eye on the face image in order to perform line-of-sight measurement with a simple configuration.

In the line-of-sight measurement device according to the second aspect, a positional relationship between the imaging unit and the light illumination unit, a positional relationship between the imaging unit and the eye, and parameters relating to the imaging unit may satisfy a predetermined constraint for determining that an imaging direction of the imaging unit and a light illumination direction of the light illumination unit are coaxial.

In the line-of-sight measurement device according to the second aspect, the pupil center calculation unit may calculate an angle formed by a line segment connecting the three-dimensional coordinates of the eyeball center in the camera coordinate system and the three-dimensional coordinates of the corneal curvature center of the camera coordinate system and a line segment connecting the three-dimensional coordinates of the eyeball center in the camera coordinate system and three-dimensional coordinates of the imaging unit, on the basis of the optical axis vector and the three-dimensional coordinates of the eyeball center in the camera coordinate system, acquire a predetermined angle correction amount corresponding to the calculated angle, calculate a vector connecting the three-dimensional coordinates of the eyeball center in the camera coordinate system and the three-dimensional coordinates of the apparent pupil center in the camera coordinate system, on the basis of the three-dimensional coordinates of the eyeball center in the camera coordinate system, the optical axis vector, and the angle correction amount, and obtain the three-dimensional coordinates of the apparent pupil center in the camera coordinate system, on the basis of the calculated vector, the three-dimensional coordinates of the eyeball center in the camera coordinate system, and a predetermined three-dimensional eyeball model.

As described above, the line-of-sight measurement device according to the aspect of this disclosure is capable of accurately obtaining the image coordinates of the corneal reflection image on the face image or the image coordinates of the pupil center in order to perform line-of-sight measurement with a simple configuration.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A line-of-sight measurement device comprising:
    an imaging unit that images a face of a subject to be observed;
    a light illumination unit that illuminates light to an eye of the subject to be observed;
    a camera coordinate system eyeball center coordinate calculation unit that estimates three-dimensional coordinates of an eyeball center in a camera coordinate system, from a face image representing the face imaged by the imaging unit;
    a pupil center calculation unit that estimates three-dimensional coordinates of an apparent pupil center in the camera coordinate system, from a pupil center position of the eye on the face image;
    an eyeball position orientation estimation unit that calculates a three-dimensional optical axis vector toward a three-dimensional position of the pupil center from a three-dimensional position of the eyeball center, in the camera coordinate system, on the basis of the three-dimensional coordinates of the eyeball center in the camera coordinate system and the three-dimensional coordinates of the apparent pupil center in the camera coordinate system;
    a corneal reflection image calculation unit that obtains three-dimensional coordinates of a corneal reflection image in the camera coordinate system, on the basis of the three-dimensional coordinates of the eyeball center in the camera coordinate system, the optical axis vector, and a predetermined three-dimensional eyeball model; and
    an image coordinate calculation unit that estimates image coordinates of a corneal reflection image on the face image, from the three-dimensional coordinates of the corneal reflection image in the camera coordinate system.

2. The line-of-sight measurement device according to claim 1, wherein
    a positional relationship between the imaging unit and the light illumination unit, a positional relationship between the imaging unit and the eye, and parameters relating to the imaging unit satisfy a predetermined constraint for determining that an imaging direction of the imaging unit and a light illumination direction of the light illumination unit are coaxial.

3. The line-of-sight measurement device according to claim 2, wherein
    the eyeball position orientation estimation unit
        calculates an angle formed by a line segment connecting the three-dimensional coordinates of the apparent pupil center in the camera coordinate system and the three-dimensional coordinates of the eyeball center in the camera coordinate system and a line segment connecting the three-dimensional coordinates of the eyeball center in the camera coordinate system and three-dimensional coordinates of the imaging unit, acquires a predetermined angle correction amount corresponding to the angle, and calculates the three-dimensional optical axis vector toward the three-dimensional position of the pupil center from the three-dimensional position of the eyeball center in the camera coordinate system, on the basis of a vector connecting the three-dimensional coordinates of the eyeball center in the camera coordinate system and the three-dimensional coordinates of the apparent pupil center in the camera coordinate system, the acquired angle correction amount, the calculated angle, and the three-dimensional coordinates of the eyeball center in the camera coordinate system.

4. A line-of-sight measurement device comprising:

an imaging unit that images a face of a subject to be observed;

a light illumination unit that illuminates light to an eye of the subject to be observed;

a camera coordinate system eyeball center coordinate calculation unit that estimates three-dimensional coordinates of an eyeball center in a camera coordinate system, from a face image representing the face imaged by the imaging unit;

a corneal reflection image calculation unit that estimates three-dimensional coordinates of a corneal reflection image in the camera coordinate system, from a position of the corneal reflection image of the eye on the face image;

an eyeball position orientation estimation unit that calculates a three-dimensional optical axis vector toward a three-dimensional position of a corneal curvature center from a three-dimensional position of the eyeball center, in the camera coordinate system, on the basis of the three-dimensional coordinates of the eyeball center in the camera coordinate system and the three-dimensional coordinates of the corneal reflection image in the camera coordinate system;

a pupil center calculation unit that obtains three-dimensional coordinates of an apparent pupil center in the camera coordinate system, on the basis of the three-dimensional coordinates of the eyeball center in the camera coordinate system, the optical axis vector, and a predetermined three-dimensional eyeball model; and an image coordinate calculation unit that estimates image coordinates of a pupil center on the face image, from the three-dimensional coordinates of the apparent pupil center in the camera coordinate system.

5. The line-of-sight measurement device according to claim 4, wherein a positional relationship between the imaging unit and the light illumination unit, a positional relationship between the imaging unit and the eye, and parameters relating to the imaging unit satisfy a predetermined constraint for determining that an imaging direction of the imaging unit and a light illumination direction of the light illumination unit are coaxial.

6. The line-of-sight measurement device according to claim 5, wherein the pupil center calculation unit calculates an angle formed by a line segment connecting the three-dimensional coordinates of the eyeball center in the camera coordinate system and the three-dimensional coordinates of the corneal curvature center of the camera coordinate system and a line segment connecting the three-dimensional coordinates of the eyeball center in the camera coordinate system and three-dimensional coordinates of the imaging unit, on the basis of the optical axis vector and the three-dimensional coordinates of the eyeball center in the camera coordinate system, acquires a predetermined angle correction amount corresponding to the calculated angle, calculates a vector connecting the three-dimensional coordinates of the eyeball center in the camera coordinate system and the three-dimensional coordinates of the apparent pupil center in the camera coordinate system, on the basis of the three-dimensional coordinates of the eyeball center in the camera coordinate system, the optical axis vector, and the angle correction amount, and obtains the three-dimensional coordinates of the apparent pupil center in the camera coordinate system, on the basis of the calculated vector, the three-dimensional coordinates of the eyeball center in the camera coordinate system, and a predetermined three-dimensional eyeball model.

* * * * *